US006666889B1

United States Patent
Commarmond

(10) Patent No.: US 6,666,889 B1
(45) Date of Patent: Dec. 23, 2003

(54) INTERSOMATIC IMPLANT FOR SAGITTAL INSERTION AND SUITABLE FOR BEING OFFSET TRANSVERSELY IN THE FRONTAL PLANE

(75) Inventor: Jacques Commarmond, Vichy (FR)

(73) Assignee: Scient'x (societe anonyme), Guyancourt (FR)

(*) Notice: Subject to any disclaimer, the term of this patent is extended or adjusted under 35 U.S.C. 154(b) by 0 days.

(21) Appl. No.: 09/889,190

(22) PCT Filed: Jan. 26, 2000

(86) PCT No.: PCT/FR00/00176
§ 371 (c)(1),
(2), (4) Date: Jul. 12, 2001

(87) PCT Pub. No.: WO00/44318
PCT Pub. Date: Aug. 3, 2000

(30) Foreign Application Priority Data

Jan. 26, 1999 (FR) .......................................... 99 00982

(51) Int. Cl.⁷ .................................................. A61F 2/44
(52) U.S. Cl. ..................................... 623/17.11; 606/61
(58) Field of Search ........................... 623/16.11, 17.11, 623/17.16, 17.12–17.15; 606/60, 61

(56) References Cited

U.S. PATENT DOCUMENTS 5,609,635 A * 3/1997 Michelson .................. 606/61
6,224,631 B1 * 5/2001 Kohrs ...................... 623/17.11

FOREIGN PATENT DOCUMENTS

| EP | 0493698 | 7/1992 |
| EP | 0599419 | 6/1994 |
| EP | 0834295 | 4/1998 |
| FR | 2724312 | 3/1996 |
| WO | WO9614809 | 5/1996 |
| WO | WO9723174 | 7/1997 |
| WO | WO9817209 | 4/1998 |

* cited by examiner

Primary Examiner—David J. Isabella
Assistant Examiner—Urmi Chattopadhyay
(74) Attorney, Agent, or Firm—Ladas & Parry

(57) ABSTRACT

A lumbar intersomatic implant for insertion into the discal space between two adjacent vertebrae for reestablishing the anatomical intervertebral space, the implant being in the form of a generally rectangular cage having two sagittal walls interconnected by at least an anterior transverse wall and a posterior transverse wall, the walls defining between them an open volume for filling with bone. An "outer" one of the sagittal walls of the implant presents a top rim and a bottom rim each shaped to present at least one retention edge extending substantially in the sagittal plane, making insertion via a posterior path possible, and an outer face arranged to present a penetration assisting shape enabling the cage to be offset transversely to a locking position in the discal space, which position is obtained by the retention edge preventing the cage from being reversed transversely.

16 Claims, 2 Drawing Sheets

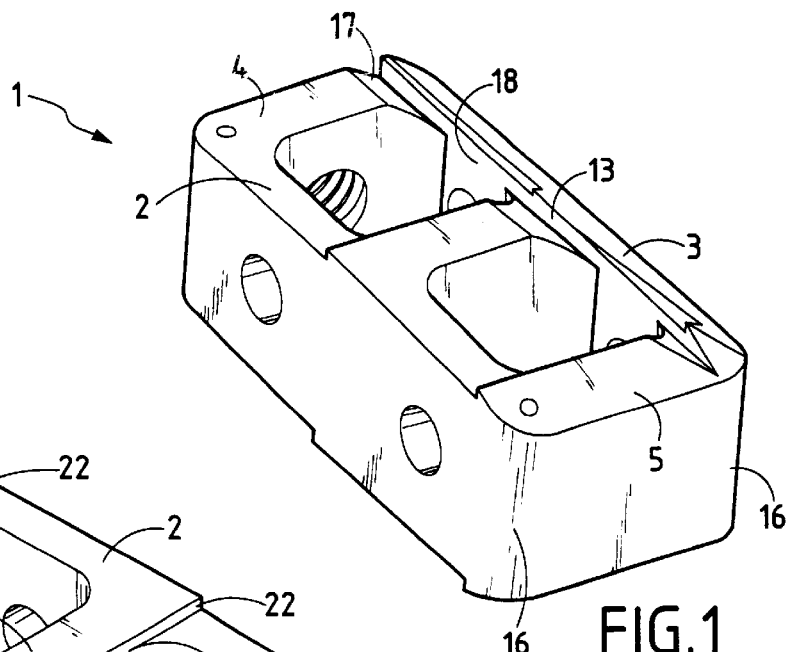
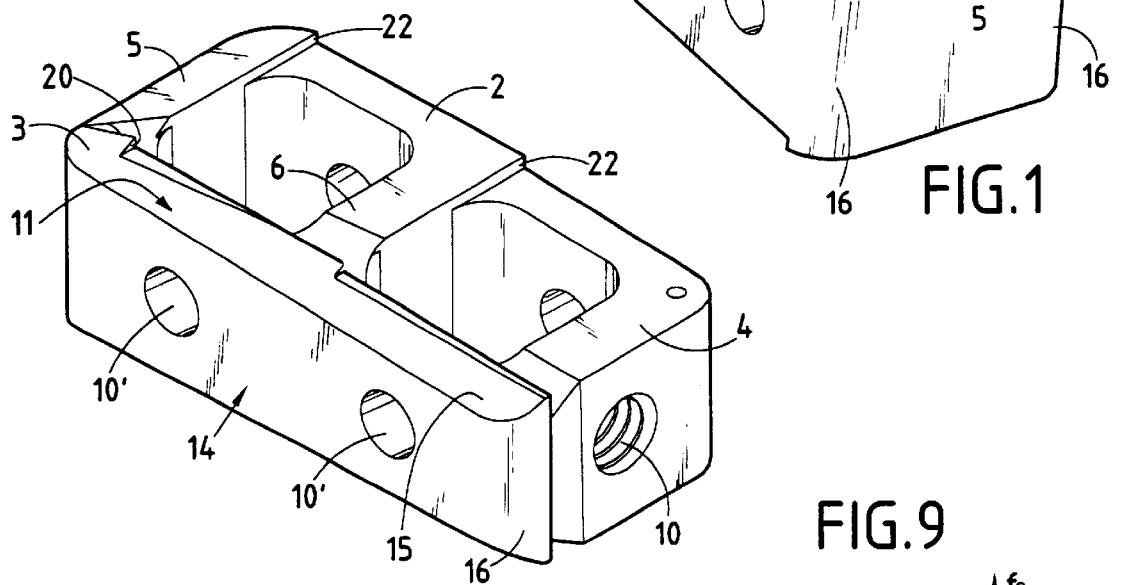
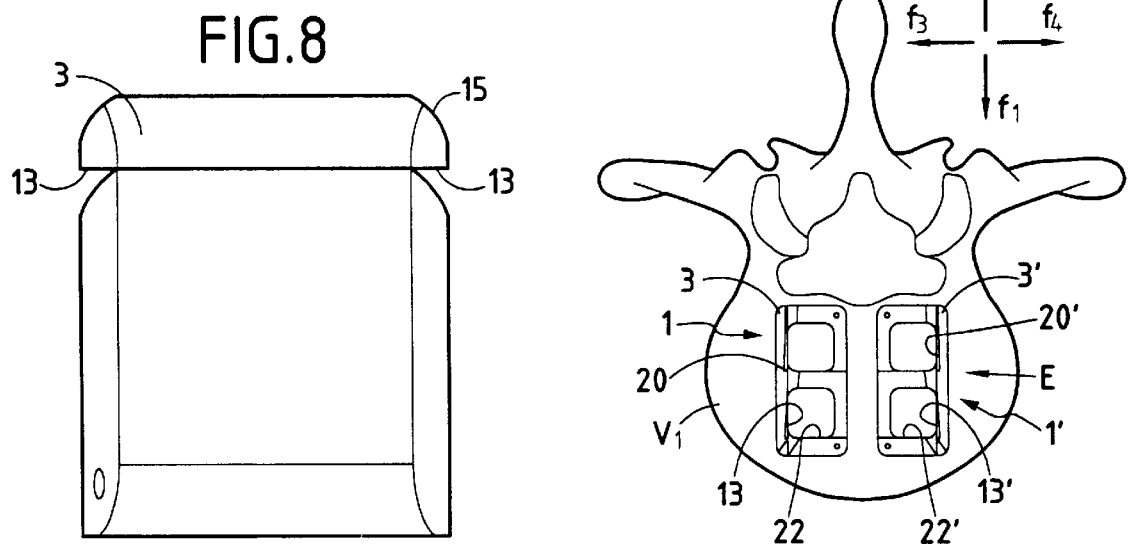

US 6,666,889 B1

INTERSOMATIC IMPLANT FOR SAGITTAL INSERTION AND SUITABLE FOR BEING OFFSET TRANSVERSELY IN THE FRONTAL PLANE

TECHNICAL FIELD

The present invention relates to an intersomatic implant for insertion in the discal space defined between two adjacent vertebrae in order to reestablish an appropriate height between the vertebrae and ensure that bone fusion takes place between said adjacent vertebrae.

The invention sets out more particularly to reestablish the discal space in the lumbar portion of the spinal column of a patient.

PRIOR ART

In the state of the art, it is known to insert an intersomatic implant in the discal space defined between two adjacent vertebrae. Numerous embodiments of such intersomatic implants have been proposed in the prior art. For example, patent FR 2 724 312 discloses a lumbar intersomatic implant in the form of a cage having two sagittal walls interconnected by an anterior transverse wall and a posterior transverse wall. Between them, the walls define an open volume for receiving spongy bone material for enhancing bone fusion between the two vertebrae. Such an implant presents an enlarged end portion giving it a kidney-shaped configuration making it possible to obtain a relatively large bearing area. Furthermore, the bottom and top edges of the walls of the cage are provided with spikes to retain the cage by anchoring in the bone of each adjacent vertebra. The design of such an implant is intended to avoid any migration of the implant either transversely or longitudinally once it has been inserted in a sagittal direction.

Although such an implant presents a large bearing area because of its kidney shape, it suffers from the drawback of sometimes requiring an approach path that is relatively large. It is also known, in particular from document EP 0 493 698 to provide a cage of generally rectangular shape offering the advantage of reducing the size of the approach path. Nevertheless, it is found that under certain conditions it is difficult to place the implant in the intervertebral space in a position enabling it to provide good stability between adjacent vertebrae, even though such stability is essential in order to obtain good bone fusion.

SUMMARY OF THE INVENTION

The Applicant has had the merit of designing a lumbar intersomatic implant adapted to provide the possibility of being placed in a position suitable for obtaining improved stability between two adjacent vertebrae by increasing the area of the support polygon, while nevertheless naturally also limiting the size of the approach path.

The object of the invention is thus to satisfy this need by proposing a lumbar intersomatic implant for insertion between two adjacent vertebrae via a limited approach path while nevertheless enabling it to be positioned in the vicinity of the side edges of the vertebrae in order to increase the area of the support polygon, and consequently to increase stability between said adjacent vertebrae.

To achieve such an object, the implant of the invention is a lumbar intersomatic implant for insertion into the discal space between two adjacent vertebrae for reestablishing the anatomical intervertebral space, the implant being in the form of a generally rectangular cage having two sagittal walls interconnected by at least an anterior transverse wall and a posterior transverse wall, the walls defining between them an open volume for filling with bone.

According to the invention, an "outer" one of the sagittal walls of the implant presents:

a top rim and a bottom rim each shaped to present at least one retention edge extending substantially in the sagittal plane, making insertion via a posterior path possible; and an outer face arranged to present a penetration-assisting shape enabling the cage to be offset transversely to a locking position in the discal space, which position is obtained by the retention edge preventing the cage from being reversed transversely.

In accordance with the invention, the intersomatic implant is inserted into the intervertebral space in a direction that is substantially parallel to the sagittal plane and it is thus designed to be capable of being moved transversely so as to come into the vicinity of the side edges of the vertebrae, thereby increasing the area of the support polygon between said two vertebrae.

A particularly advantageous application of the invention lies in being inserted via a single posterior unilateral path that is less damaging to the patient than the conventional broad approach path. It is possible to envisage inserting one or two lumbar intersomatic implants via a unilateral posterior path while nevertheless obtaining increased stability between said adjacent vertebrae. Installing such an implant via a unilateral posterior path makes it possible to avoid interrupting the structure of the spinous processes, to avoid forcing the paravertebral muscles hard and long, and to avoid inflicting circumferential fibrosis.

Various other characteristics appear from the following description made with reference to the accompanying drawings which show embodiments and implementations of the invention as non-limiting examples.

BRIEF DESCRIPTION OF THE DRAWINGS

FIG. 1 is a three-quarter front perspective view of an embodiment of an implant of the invention.

FIG. 2 is an opposite three-quarter rear perspective view of the implant shown in FIG. 1.

FIG. 8 is a profile view showing a characteristic detail of a variant embodiment of the invention.

FIG. 9 is a plan view of an example of lumbar intersomatic implants put into place in a discal space.

BEST MANNER OF PERFORMING THE INVENTION

Figure 5:
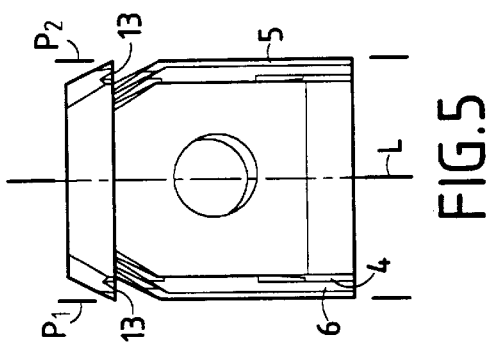
FIG. 5 is a rear profile view of an implant of the invention.

As can be seen more precisely in FIGS. 1 to 7, the lumbar intersomatic implant of the invention is in the form of a cage 1 which is generally rectangular in shape, and is designed to be inserted in the discal space between two adjacent vertebrae. The cage 1 has a "medial" or "inner" first sagittal wall 2 and a "lateral" or "outer" second sagittal wall 3 extending substantially parallel to each other and to the "antero-posterior" or "sagittal" plane S. The sagittal walls 2 and 3 are interconnected by a "posterior" transverse wall 4 and by an "anterior" transverse wall 5 extending parallel to each other and to a vertical transverse plane T perpendicular to the sagittal plane S.

In a preferred embodiment shown in the drawings, the cage 1 has at least one intermediate transverse wall 6 connected to the sagittal walls 2 and 3 and extending parallel to the transverse walls 4 and 5 at a distance therefrom. In the example shown, the intermediate transverse wall 6 constitutes a middle wall relative to the transverse walls 4 and 5. The cage 1 thus has two internal volumes 7 opening out into a top face 8 and a bottom face 9 of the cage. The volumes 7 are for filling with spongy bone for intersomatic fusion. In conventional manner, the posterior transverse wall 4 has a hole 10 that opens out into the volume 7 and that is optionally tapped. The hole 10 is for receiving a tool for holding and positioning the cage between the vertebrae, and subsequently serves to encourage bone fusion. According to a preferred characteristic, each sagittal wall 2, 3 is provided with two through holes 10' each communicating with one of the volumes 7.

The "outer" sagittal wall 3 has a top rim 11 and a bottom rim 12 extending respectively from the top and bottom faces 8 and 9. In accordance with the invention, each rim 11, 12 is arranged to present at least one retention edge 13 extending in a plane parallel to the sagittal plane S, as can be seen clearly in FIG. 3. Given the extension of the retention edge 13 in the sagittal plane S, the cage can be moved in both directions "sagittally" as represented by arrows $f_1$ and $f_2$ perpendicularly to the transverse plane T. In the example shown, the insertion direction $f_1$ (opposite to the direction $f_2$) is the direction in which the anterior transverse wall 5 is situated downstream relative to the posterior transverse wall 4.

According to another characteristic of the invention, the outer sagittal wall 3 has an outer face 14 arranged to present a shape 15 for assisting penetration and allowing the cage to be offset transversely in a direction $f_3$ perpendicular to the sagittal plane S, and for which the outer wall 3 is downstream relative to the inner wall 2. This penetration-helping shape 15 allows the cage to be moved transversely in the direction $f_3$ until it reaches a blocking position obtained by the retention edge 13 preventing the cage from reversing transversely in the direction $f_4$ opposite to the direction $f_3$. As can be seen more clearly in FIGS. 4 and 5, each retention edge 13 formed on the outer sagittal wall 3 is extended transversely outwards by a shape 15 for assisting penetration that is constituted in the example shown by a chamfer such that said sagittal wall 3 presents a frustoconical profile in the transverse plane T with the small base thereof being formed by the outer face of the sagittal wall 3. Naturally, the outer face 14 of the sagittal wall could be given a different profile while still allowing the cage to be inserted in the direction $f_3$. For example, each chamfer could be replaced by a rounded profile 15, as shown in FIG. 8. Similarly, and as can be seen more clearly in FIGS. 1 and 2, the outer face 14 of the outer sagittal wall 3 joins the transverse walls 4 and 5 via rounded corners 16. Similarly, the inner sagittal wall 2 joins the transverse walls 4 and 5 via rounded corners 16 so that the entire cage has rounded corners.

Preferably, each retention edge 13 is obtained by chamfering performed in the connection portions 17 of the transverse walls 4, 5, and 6 where they join the outer sagittal wall 3. Thus, each retention edge 13 is constituted by the top longitudinal portion of the inner face 18 of the outer sagittal wall 3 thus forming a tooth, a point, or a margin that projects relative to the transverse walls 4, 5, and 6. In the example shown in the drawings, the retention edge 13 extends continuously over the entire length of the cage, from the posterior wall 4 to the anterior wall 5. Naturally, it could be envisaged that the retention edge 13 extends over a fraction only of the length of the cage as one or more segments. Generally, the outer sagittal wall 3 can be arranged to present a plurality of retention edges 13 that are offset from one another, each extending in a plane parallel to the sagittal plane S. Furthermore, each retention edge 13 can present a profile in the sagittal plane S that is rectilinear or convex.

In a preferred embodiment, the cage 1 is symmetrical about a longitudinal midplane L perpendicular to the sagittal plane S and to the transverse plane T. Thus, after a cage 1 has been turned upside-down about a longitudinal axis, it can take up a position that is symmetrical to that occupied by another, like cage.

In a first embodiment, each retention edge 13 extends substantially in top and bottom end extension planes $P_1$ and $P_2$ from the walls of the cage. Thus, as can be seen in FIG. 5, the retention edges 13 do not project beyond the top and bottom planes $P_1$ and $P_2$ parallel to the longitudinal plane L in which the extreme edges of the walls 2, 4, 5, or 6 extend. It should be observed that it could be envisaged having each retention edge 13 projecting from the bottom and top extreme extension planes $P_1$ and $P_2$ of the walls 2, 4, 5, or 6 so as to give the cage a distracting effect while it is inserted into the intervertebral space. In this particular embodiment, each retention edge 13 extends beyond the rims of the transverse walls 4, 5, 6 and the inner sagittal wall 2.

Figure 6:
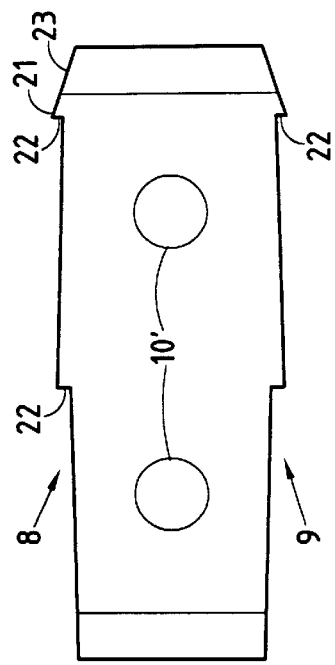
FIG. 6 is a "bottom" lateral profile view, relative to the plan view of FIG. 3.
Figure 3:
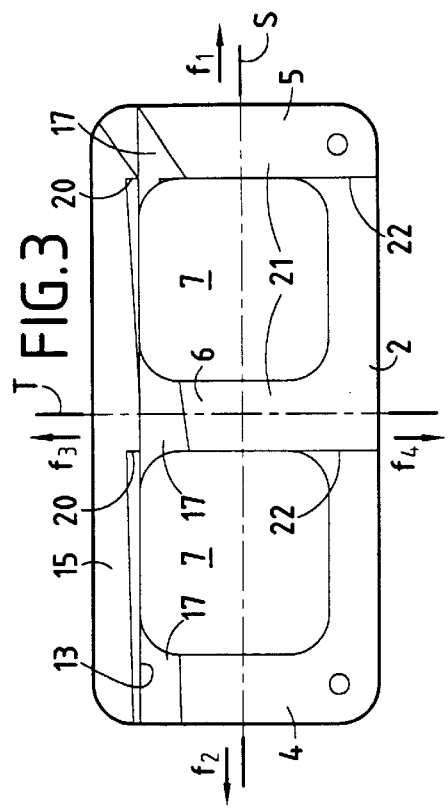
FIG. 3 is a plan view of an implant of the invention.
Figure 7:
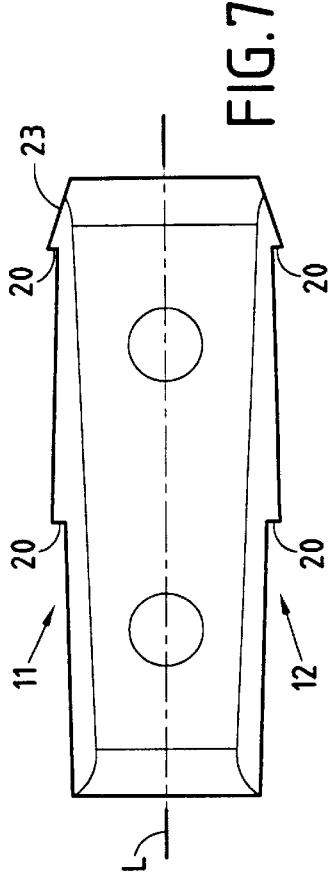
FIG. 7 is a "top" lateral profile view, relative to the plan view of FIG. 3.
Figure 4:
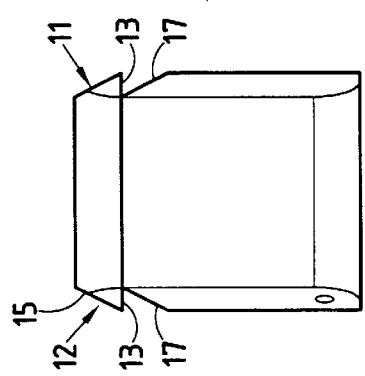
FIG. 4 is a front profile view of an implant of the invention.

According to another characteristic of the invention, each retention edge 13 is locally cut to define at least one, and in the example shown two steps 20 forming abutments that opposite withdrawal of the cage in the sagittal plane in the direction $f_2$ (FIGS. 3 and 7). Similarly, at least one of the transverse walls, and in the example shown the anterior wall 5 and the intermediate wall 6, presents bottom and top rims 21 each arranged to present at least one retention tooth or stop 22 preventing the cage from being reversed in the direction $f_2$ (FIGS. 3 and 6). In the example shown, each retention tooth 22 extends in a transverse plane common to that in which a step 20 extends. As can be seen more clearly from FIGS. 2, 3, and 6, each retention tooth 22 is constituted by the top portion of the inner face of the anterior and intermediate transverse walls 5 and 6. Thus, the rims of the sagittal walls 2 and 3 between the inner faces of the anterior and intermediate transverse walls 5 and 6, and the rim of the intermediate transverse wall 6, are cut obliquely so as to reveal the retention teeth 22 and the steps 20 so that the cage presents a frustoconical profile in the sagittal plane S (FIG. 6) over this portion of its length. Similarly, the rim of the posterior transverse wall 4 and the rims of the sagittal walls 2 and 3 between the inner face of the intermediate transverse wall 6 and the outer face of the posterior transverse wall 4 are cut on a plane substantially parallel to the longitudinal plane L so that the cage presents a profile over the fraction of its length that is substantially rectangular in the sagittal plane S. Furthermore, each rim 23 of the anterior transverse wall 5 is cut obliquely so that the profile of this wall in the sagittal plane is frustoconical with its smaller base formed by the outer face of the wall 5.

In a preferred embodiment and as can be seen more clearly in FIGS. 5 and 7, the transverse walls 4, 5, and 6 are of determined different heights in the sagittal plane S so as to define a slope that matches the physiological shape of the intervertebral space.

As can be seen in FIG. 9, the cage 1 of the invention is for insertion in the discal space E defined between two adjacent vertebrae, only one of which V₁ is shown. The cage 1 has the special feature of being suitable for being inserted into the discal space in a direction that is substantially parallel to its sagittal plane in the direction of arrow $f_1$ and then of being offset transversely in the direction of arrow $f_3$ until it reaches a locking position in the discal space provided by the retention edges 13 becoming anchored in the vertebral plates, thus preventing the cage from being withdrawn in the opposite direction $f_4$. Similarly, the cage 1 can be locked in the sagittal plane in the direction $f_2$ by the steps 20 and the teeth 22 co-operating with the vertebral plates.

SUSCEPTIBILITY OF INDUSTRIAL APPLICATION

The subject matter of the invention is particularly suitable for enabling intersomatic lumbar arthrodesis to be performed with two cages 1 being inserted via a unilateral posterior path. With this technique, a posterior unilateral approach path is made in the patient, and a first cage 1 is inserted along said path into the discal space by being moved substantially in its sagittal plane S and then offset transversely. Such an implant can thus be placed in the discal space on the opposite side to the approach path. A second cage 1' can then be inserted using the same approach path, being oriented symmetrically relative to the first cage 1. The cage 1' is identical to the cage 1, merely being turned upside-down prior to being inserted into the discal space. As can be seen clearly in FIG. 9, the cages 1, 1' are positioned in such a manner that the outer sagittal walls 3, 3' lie adjacent to the outer sides of the vertebral plates. Given the symmetrical position of the cage 1' relative to the cage 1, the cage 1' is prevented from moving in the direction $f_3$ by the retention edges 13', while the cage 1' is prevented from moving in the sagittal plane S in the direction $f_1$ by the steps 20' and the teeth 22'.

What is claimed is:

1. A lumbar intersomatic implant for insertion into a discal space between two adjacent vertebrae for reestablishing the anatomical intervertebral space, the implant being a generally rectangular cage having inner and outer sagittal walls interconnected by at least an anterior transverse wall and a posterior transverse wall, the sagittal and transverse walls defining between them an open volume for filling with bone, wherein the outer sagittal wall of the implant presents:
a top rim and a bottom rim each shaped to present at least one retention edge extending substantially in the sagittal plane, facilitating the insertion into the discal space via a posterior path; and
an outer face comprising a penetration-assisting shape enabling the cage to be offset transversely to a locking position in the discal space, which position is maintained by the at least one retention edge preventing the cage from being reversed transversely.

2. An implant according to claim 1, wherein the cage is symmetrical about a longitudinal midplane intersecting the sagittal walls, so as to enable the cage to occupy a position that is symmetrical to that of another, second cage by being turned upside-down.

3. An implant according to claim 1, wherein the cage has at least one intermediate transverse wall connected to the sagittal walls and extending at a distance from the anterior and posterior transverse walls to define separate respective volumes for filling with bone.

4. An implant according to claim 1, wherein the at least one retention edge projects from bottom and top extreme extension planes of the transverse walls.

5. An implant according to claim 1, wherein at least one retention edge is formed by chamfering connection portions of the transverse walls where the transverse wall join the outer sagittal wall.

6. An implant according to claim 1, wherein a chamfer extends transversely outwards from each retention edge such that the sagittal wall presents a frustoconical profile.

7. An implant according to claim 6, wherein each retention edge extends along the rims of the outer sagittal wall in a continuous manner.

8. An implant according to claim 7, wherein each retention edge presents a profile that is rectilinear in the sagittal plane.

9. An implant according to claim 6, wherein each retention edge extends as a plurality of segments between the anterior transverse wall and the posterior transverse wall.

10. An implant according to claim 9, wherein each retention edge presents a profile that is rectilinear in the sagittal plane.

11. An implant according to claim 9, wherein each retention edge presents a profile that is convex in the sagittal plane.

12. An implant according to claim 7, wherein each retention edge presents a profile that is convex in the sagittal plane.

13. An implant according to claim 1, wherein each retention edge is cut locally substantially perpendicular to the sagittal plane to define at least one step configured to oppose withdrawal of the cage from the locking position in the sagittal plane.

14. An implant according to claim 1, wherein at least one of the transverse walls has a top edge and a bottom edge, each edge comprising at least one retention tooth configured to prevent the cage from being withdrawn from the locking position in the sagittal plane.

15. An implant according to claim 14, wherein the transverse walls present different determined heights in the sagittal plane so that between them they define a slope which is adapted to a physiological shape of the discal space.

16. An implant according to claim 1, wherein the sagittal walls are provided with through holes opening out to the inside of the volume for filling with bone in order to encourage bone fusion.

\* \* \* \* \*